United States Patent [19]

Crossland

[11] Patent Number: 5,043,506
[45] Date of Patent: Aug. 27, 1991

[54] PROCESS FOR THE ALKYLATION OF ORGANIC AROMTIC COMPOUNDS IN THE PRESENCE OF INERT ALIPHATIC COMPOUNDS

[76] Inventor: Clifford S. Crossland, P.O. Box 890509, Houston, Tex. 77289-0509

[21] Appl. No.: 583,161

[22] Filed: Sep. 17, 1990

[51] Int. Cl.$^5$ ............................................. C07C 2/64
[52] U.S. Cl. ..................... 585/449; 585/467; 585/446; 203/DIG. 6
[58] Field of Search ................. 585/449, 446, 467; 203/DIG. 6

[56] References Cited

U.S. PATENT DOCUMENTS

| | | | |
|---|---|---|---|
| 2,550,413 | 4/1951 | Gislon | 585/449 |
| 3,950,448 | 4/1976 | Witt | 585/449 |
| 4,215,011 | 7/1980 | Smith, Jr. | 252/426 |
| 4,232,177 | 11/1980 | Smith, Jr. | 585/324 |
| 4,242,530 | 12/1980 | Smith, Jr. | 585/510 |
| 4,250,052 | 2/1981 | Smith, Jr. | 252/426 |
| 4,302,356 | 11/1981 | Smith, Jr. | 252/426 |
| 4,307,254 | 12/1981 | Smith, Jr. | 568/647 |
| 4,343,957 | 8/1982 | Sartorio et al. | 585/449 |
| 4,443,559 | 4/1984 | Smith, Jr. | 502/527 |
| 4,849,569 | 7/1989 | Smith, Jr. | 585/446 |
| 4,918,244 | 4/1990 | Nelson et al. | 568/698 |
| 4,950,834 | 8/1990 | Arganbright et al. | 585/446 |

Primary Examiner—Anthony McFarlane
Assistant Examiner—Nhat Phan
Attorney, Agent, or Firm—Kenneth H. Johnson

[57] ABSTRACT

An improvement in the operation to a catalytic distillation process for the alkylation of organic aromatic compounds with an olefin contained wherein aliphatic compounds are contained in either the olefin feed stream, the aromatic feed stream or both is disclosed. Aliphatic compounds are added to the upper portion of a secondary distillation column reactor wherein aromatic is being reacted with unreacted olefin from a primary distillation column reactor to polish the conversion of olefin. The additional aliphatic compound produces an equilibrium in the secondary column wherein unreacted aromatic and alkylation product are recovered as bottoms which may be recycled to the primary distillation column reactor.

11 Claims, 1 Drawing Sheet 5,043,506

PROCESS FOR THE ALKYLATION OF ORGANIC AROMTIC COMPOUNDS IN THE PRESENCE OF INERT ALIPHATIC COMPOUNDS

BACKGROUND OF THE INVENTION

1. Field of the Invention

The present invention relates to a process for the alkylation of organic aromatic compounds. More particularly the invention relates to a process for the concurrent alkylation and distillation of reaction components (reactants and products) in a catalyst bed wherein the catalyst also serves as the distillation structure. More particularly the invention relates to a method of operating an aromatic alkylation process wherein the olefin is contained in a stream having "inert" aliphatic compounds therein and wherein the aromatic stream also contains aliphatic compounds.

2. Related Art

Ethyl benzene and cumene have traditionally been produced by the reaction of benzene and the respective olefin, i.e., ethylene and propylene in the presence of an acidic catalyst. In some known processes the catalyst is highly corrosive and has a relatively short life, e.g., $AlCl_3$, $H_3PO_4$ on clay, $BF_3$ on alumina, and others require periodic regeneration, e.g., molecular sieves. The exothermicity of the reaction and the tendency to produce polysubstituted benzene require low benzene conversions per pass with large volume recycle in conventional processes.

Recently a new method of carrying out catalytic reactions has been developed, wherein the components of the reaction system are concurrently separable by distillation, using the catalyst structures as the distillation structures. Such systems are described variously in U.S. Pat. Nos. 4,215,011; 4,232,177; 4,242,530; 4,250,052; 4,302,356; and 4,307,254 commonly assigned herewith. Briefly, a structure described there is a cloth belt with a plurality of pockets spaced along the belt, which is then wound in a helix about a spacing material such as stainless steel knitted mesh. These units are then disposed in the distillation column reactor. In addition, commonly assigned U.S. Pat. No. 4,443,559 discloses a variety of catalyst structures for this use and is incorporated herein.

More recently the method has been applied to aromatic alkylation as in U.S. Pat. No. 4,849,569 and copending and commonly assigned application Ser. Nos. 07/122,485 and 07/264,844. As noted therein the olefin feed to the alkylation process often contains aliphatic compounds which have a boiling range in and around the specific olefin to be used in the reaction. These aliphatic compounds are inert and simply pass through the distillation column reactor. However, in the final separation of unreacted aromatic compound (which is usually recycled to the reactor as reflux) from the inerts, it has been found that such separation can require extensive capital investment in the form of additional distillation trays. Additionally, it has sometimes been found to be advantageous to include a second separate distillation column fixed bed reactor or fixed bed reactor to polish or finish the reaction of all the olefin with aromatic.

Advantages of the present invention include a better utilization of the aromatic compound and more complete reaction of the olefin.

SUMMARY OF THE INVENTION

Briefly, the present invention is an improvement in the operation of a distillation column reactor in the "catalytic distillation" production of alkylated aromatic compounds. In normal refinery streams containing olefins useful for the alkylation of organic aromatic compounds there are usually included some aliphatic compounds boiling in the same range as the olefin to be used. Additionally the aromatic stream may contain up to 0.15 per cent aliphatics as in nitration grade benzene.. In nitration grade benzene these aliphatics normally consist of $C_7$ and $C_8$ compounds which boil at substantially the same temperature as the benzene. While these aliphatic compounds are "inert" in the reaction zone, they increase the loading in the distillation zone where the aromatic is separated for recycle to the reaction zone.

In addition there may be some carry over of unreacted olefin from the primary reaction zone into the distillation zone along with the unreacted aromatic compound and the aliphatic compounds. In order to insure complete reaction of the olefin, a secondary, or polishing, reaction zone is provided having another distillation reaction structure. Briefly, the overhead from the primary distillation reaction zone containing unreacted aromatic compound, any unreacted olefin, and the aliphatic compounds, is partially condensed to liquify primarily the aromatic compound along with most of the aliphatic compounds. The liquid and gas streams are then contacted in a secondary distillation zone to complete the reaction. Above the secondary distillation reaction zone is a second distillation zone into which additional aliphatic compounds are injected as liquid reflux to drive the aromatic compound toward the reaction zone of the column. Thus only aliphatic compounds are taken overhead in the secondary distillation column reactor with the aromatic compound and alkylation product produced therein removed as bottoms. The bottoms from the second distillation column reactor are then recycled to the first reactions distillation column where the alkylation product is recovered with the bottoms there, and the aromatic compound contributes to the molar excess required for the primary reaction.

The aliphatic compounds are generally $C_3$-$C_8$ or 9 normal or branched alkanes. A preferable grouping comprises propane, butane, pentane, hexane, isohexane or mixtures thereof.

The advantages of the "catalytic distillation" are thus taken while improving the utilization of the olefin without undue loss of the aromatic compound.

DETAILED DESCRIPTION

Figure 1:
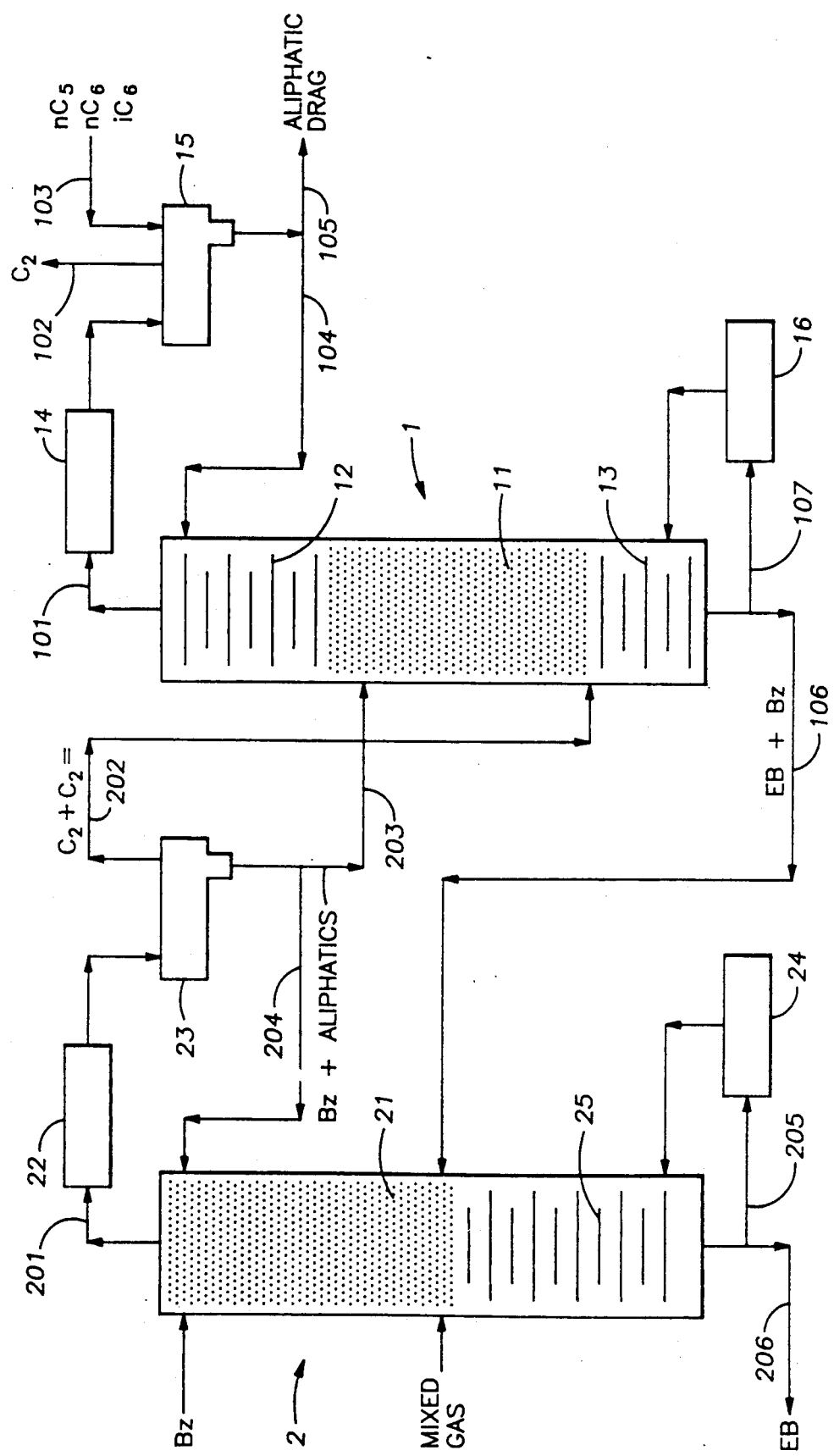
FIG. 1 is a simplified flow diagram of the preferred embodiment of the present invention as used in the production of ethyl benzene.

The olefins may be $C_2$ to $C_{12}$ olefins, preferably $C_2$ to $C_8$ olefins, including normal and branched forms thereof. For example, suitable olefins are ethylene, propylene, butylene, isobutylene, 1-pentene, isopentene, 1-hexene, 2-hexene, 2,3-dimethyl-1-pentene, 1-octene, diisobutylene, 1-nonene and 1-decene, dodecene and the like. The olefins may contain substituents which do not interfere with the alkylation. In one preferred embodiment the olefin is a $C_2$ to $C_4$ olefin.

The organic aromatic compounds are preferably those having a boiling point of 250°C or less under the pressure conditions of the distillation column reactor. The organic aromatic compounds include hydrocarbons of one or more rings and 6 to 20 carbon atoms which may contain substituents which do not interfere with the alkylation including halogen (Cl, Br, F and I), OH and alkyl, cycloalkyl, aralkyl and alkaryl radicals of 1 to 10 carbon atoms. Suitable organic aromatic compounds include benzene, xylene, toluene, phenol, cresol, ethyl benzene, diethyl benzene, naphthalene, indene, phenyl bromide, 1-bromo-2-chloro-benzene, 1-bromo-4-cyclohexyl benzene, 2-bromo-1,4-dihydroxy-benzene, 1(bromo-methyl) naphthalene, 1,2-dihydronaphthalene and the like, a preferred group of compounds for use in the present process is benzene, xylene, toluene, phenol, and cresol.

Catalyst and Distillation Structure

While any suitable particulate acidic catalytic structure may be used in the distillation reaction zone, molecular sieves are preferred for their stability.

Molecular sieves are porous crystalline, three-dimensional alumina-silicates of the zeolite mineral group. The crystal skeleton is composed of silicon and aluminum atoms each surrounded by four oxygen atoms to form a small pyramid or tetrahedron (tetrahedral coordination). The term molecular sieve can be applied to both naturally occurring zeolites and synthetic zeolites. Naturally occurring zeolites have irregular pore size and are not generally considered as equivalent to synthetic zeolites. In the present invention, however, naturally occurring zeolites are acceptable so long as they are substantially pure. The balance of the present discussion shall be directed to the synthetic zeolites with the understanding that natural zeolites are considered equivalent thereto as indicated above, i.e., in so far as the natural zeolites are the functional equivalents to the synthetic zeolites.

Usually synthetic zeolites are prepared in the sodium form, that is, with a sodium cation in close proximity to each aluminum tetrahedron and balancing its charge. To date seven principal types of molecular sieves have been reported, A, X, Y, L, $\beta$, erionite, omega and mordenite. The A type have relative small pore size. By the term pore size is meant the effective pore size (diameter) rather than the free pore size (diameter). Types X and Y have larger pore size (approximately 10 A.) and differ as to the range of ratio of $Al_2O_3$ to $SiO_2$ as:

Type X- - - $Al_2O_3$ /2.0–3.0 $SiO_2$
Type Y- - - $Al_2O_3$ /3.0–6.0 $SiO_2$

Type L and other types listed above have still higher ratios of $SiO_2$ to $Al_2O_3$ The mole sieve catalysts employed in the present invention are the acid form mole sieves or exhibit acidic characteristics. The acid form of the mole sieves is commercially available, but also may be prepared by treating the mole sieves with acid to exchange Na for hydrogen. Another method to produce the acid form is to treat the mole sieve with decomposable cations (generally ammonium ions) to replace Na with the decomposable ions and thereafter to heat the mole sieve to decompose the cation, leaving the acid form. Generally the Na form mole sieve is treated with ammonium hydroxide to remove the Na and thereafter the mole sieve is heated to a temperature of about 350° C to remove of ammonia. The removal of $Na^+$ ions with $NH^+_4$ is more easily carried out than with multivalent ions as described below and these catalysts are generally more active, but less stable to heat than the multivalent cation exchange forms. Mole sieves, which have had their alkali metal reduced to low levels by partial treatment with $NH^+_4$ and partial multivalent metal cation exchange, possess increased activity and increased stability.

In addition to mole sieves which are acidic according to the Brönsted Theory those mole sieves which exhibit acidic characteristics under the Lewis Theory, for example, calcium exchanged mole sieves are suitable for the present reaction. By exchanging the univalent cations (e.g. $Na^+$) with multivalent cation, strong ionic activity is imparted. The ratio of $SiO_2$: $Al_2O_3$, valence and radius of the cation and the extent of exchange all affect the catalyst activity. In general activity increases with (1) increased $SiO_2 Al_2O_3$ ratio, (2) decreased cation radius and an increase in cation valence. The effect of replacing univalent ions (e.g. $Na^+$) with bivalent (e.g. $Ca^{++}$) is much greater than replacing the bivalent ions with cations of greater valence.

The various types of mole sieves having reduced alkali metal content are characterized as the acid form molecular sieve and are all contemplated as useful in the present invention.

It would appear that the pore size within the crystal lattice may affect the selectivity. According to one theory of molecular sieve catalytic activity, zeolite catalysis occurs primarily inside the uniform crystal cavities, consequently zeolitic catalyst activity depends on the number of aluminum atoms in the crystal and thus on the chemical composition of the crystal. Moreover, these catalytic sites are fixed within the rigid structure of the crystal, so that access to the site can be altered by altering the structure of the crystal.

The acid form mole sieves are generally produced and available as particles in the range of < 10 micron (powders) to 0.2 inch in diameter (beads).

In this form the mole sieves form too compact a bed and will not function adequately in a distillation, since there is a very large pressure drop through the bed and the free flow of internal reflux and rising vapor is impeded. Mole sieves in the shape of conventional distillation structures, such as rings, saddles, and the like may be used in the present invention. The particulate mole sieves may be employed by enclosing them in a porous container such as cloth, screen wire or polymeric mesh. The material used to make the container must be inert to the reactants and conditions in the reaction system. The cloth may be any material which meets this requirement such as cotton, fiber glass, polyester, nylon and the like. The screen wire may be aluminum, steel, stainless steel and the like. The polymer mesh may be nylon, teflon or the like. The mesh or threads per inch of the material used to make the container is such that the catalyst is retained therein and will not pass through the openings in the material. Particles of about 0.15 mm size or powders may be used and particles up to about ¼ inch diameter may be employed in the containers.

The container employed to hold the catalyst particles may have any configuration, such as the pockets disclosed in the commonly assigned patents above or the container may be a single cylinder, sphere, doughnut, cube, tube or the like.

Each container containing a solid catalytic material comprises a catalyst component. Each catalyst component is intimately associated with a spacing component which is comprised of at least 70 volume % open space up to about 95 volume % open space. This component may be rigid or resilient or a combination thereof. The combination of catalyst component and spacing component form the catalytic distillation structure. The total volume of open space for the catalytic distillation structure should be at least 10 volume % and preferably at least 20 volume % up to about 65 volume %. Thus desirably the spacing component or material should comprise about 30 volume % of the catalytic distillation structure, preferably about 30 volume % to 70 volume %. Resilient materials are preferred. One suitable such material is open mesh knitted stainless wire, known generally as demister wire or an expanded aluminum. Other resilient components may be similar open mesh knitted polymeric filaments of nylon, teflon and the like. Other materials such as highly open structures foamed material, e.g., reticulated polyurethane foam (rigid or resilient) may be formed in place or applied around the catalyst component.

In the case of larger catalyst components such as from about ¼ inch to ½ pellets, spheres, pills and the like each such larger component may be individually intimately associated with or surrounded by the spacing component as described above. It is not essential that the spacing component, entirely cover the catalyst component. It is only necessary that the spacing component intimately associated with the catalyst component will act to space the various catalyst components away from one another as described above. Thus, the spacing component provides in effect a matrix of substantially open space in which the catalyst components are randomly but substantially evenly distributed.

A preferred catalytic distillation structure for use herein comprises placing the mole sieve particles into a plurality of pockets in a cloth belt, which is supported in the distillation column reactor by open mesh knitted stainless steel wire by twisting the two together in a helical form. This allows the requisite flows and prevents loss of catalysts. The cloth may be any material which is inert in the reaction. Cotton or linen are useful, but fiber glass cloth or "Teflon" cloth are preferred.

In the following examples the catalyst packing consisted of bags in the form of a fiber glass cloth belt approximately six inches wide with narrow pockets approximately ⅜ inch wide sewn across the belt. The pockets are spaced about ¼ inch apart. These pockets are filled with the catalyst particles to form approximately cylindrical containers, and the open ends are then sewn closed to confine the particles. This belt is then twisted into a helical form to fit inside the column. Twisted in with the belt is also a strip of an open mesh knitted stainless steel wire, which serves to separate the mole sieve filled cloth pockets and provide a passage for vapor flow.

The wire mesh provides the support for the catalyst (belt) and provides some degree of vapor passage through the catalyst particles, which otherwise form a very compact bed which has a high pressure drop. Thus, the down flowing liquid is in intimate contact with the rising vapors in the column.

In commercial-scale operations, it is contemplated, catalyst packing would be made up of alternating layers of mole sieve filled cloth belts similar to the ones described above, and a spacing material which could be of any convenient, suitable substance, such as a corrugated wire screen or wire cloth or a knitted wire mesh. The layers would be arranged vertically or horizontally. For simplicity of fabrication and for better distribution of vapor flow passages, a vertical orientation is preferred. The height of section of this packing should be of any convenient dimension, from a few inches to several feet. For ease of assembly and installation, the packing would be made into sections of the desired shape and size, each section fastened together with circumferential bands of tie wires depending on its size and shape. A complete assembly in a column would consist of several sections, arranged in layers, with possibly the orientation of the catalyst-filled belts turned at right angles in successive layers to improve liquid and vapor flow distribution.

Process Configuration

Referring now to the figure there is shown a configuration of the process for the production of ethyl benzene. The main components of the system are the primary distillation column reactor, generally indicated at 2, and the secondary, or polishing, distillation column reactor indicated at 1. Pumps, valves and peripheral equipment are not shown as they are well known by those skilled in the art of distillation column design.

Catalyst as described above is loaded in the upper one-half of the primary distillation column reactor as indicated at 21 and in the middle one-third of the secondary distillation column reactor as indicated at 11. The bottom half 25 of the primary distillation column reactor contains conventional distillation structure such as inert packing or distillation trays. Likewise the upper and lower one-third of the secondary distillation column reactor contains conventional distillation structure 12 and 13 respectively.

The mixed gas containing the olefin, in this case ethylene ($C_{2=}$), is usually fed below the catalyst bed 21 in the primary distillation column reactor. The aromatic compound, nitration grade benzene (Bz) containing up to 0.15 percent $C_7-C_8$ aliphatics, is fed to the primary distillation column reactor at a point above the bed 21. The aromatic compound may be conveniently added in the reflux through flow line 204.

In order to achieve high selectivity toward monosubstitution (which is a preferred aspect of the present invention), there is a large excess of the organic aromatic compound to the olefin in the primary distillation reaction zone 21 in the range of 2 to 100 moles of benzene per mole of olefin, that is, the net molar feed ratio of aromatic organic compound: olefin may be close to 1:1, e.g, 1.2:1, although the system is operated so as to maintain a substantial molar excess of organic aromatic compound to olefin in the reaction zone.

The alkylated product, here ethyl benzene (EB), is the highest boiling material and is separated in the lower portion 25 of the primary column 2 usually as bottoms some of which may be heated in reboiler 24 and returned to the primary distillation column reactor 2 to supply any needed heat. The benzene compound is the second highest boiling component (excluding inerts) as noted above, however, by operating with a large excess of benzene in the reactor, the major portion of the olefin is reacted, thereby reducing the separation and recovery problems. The success of catalytic distillation lies in an understanding of the principles associated with distillation. First, because the reaction is occurring concurrently with distillation, the initial reaction product is removed from the reaction zone as quickly as it is formed. The removal of the alkylation product minimizes polysubstitution, decomposition of the alkylation product and/or oligomerization of the olefin. Second, because the organic aromatic compound is boiling, the temperature of the reaction is controlled by the boiling point of that component at the system pressure. The heat of the reaction simply creates more boil up, but no increase in temperature. Third, the reaction has an increased driving force because the reaction products have been removed and cannot contribute to a reverse reaction (Le Chatelier's Principle).

As a result, a great deal of control over the rate of reaction and distribution of products can be achieved by regulating the system pressure. Also, adjusting the through-put (residence time = liquid hourly space velocity$^{-1}$) gives further control of product distribution and degree of olefin conversion. The temperature in the reactor is determined by the boiling point of the liquid mixture present at any given pressure. The temperature in the lower portions of the column will reflect the constitution of the material in that part of the column, which will be higher than the overhead; that is, at constant pressure a change in the temperature of the system indicates a change in the composition in the column. To change the temperature the pressure is changed. Temperature control in the reaction zone is thus controlled by the pressure; by increasing the pressure, the temperature in the system is increased, and vice versa. It can also be appreciated that in catalytic distillation as in any distillation there is both a liquid phase (internal reflux) and a vapor phase. Thus, the reactants are partially in liquid phase which allows for a more dense concentration of molecules for reaction, whereas, the concurrent fractionation separates product and unreacted materials, providing the benefits of a liquid phase system (and a vapor phase system) while avoiding the detriment of having all of the components of the reaction system continually in contact with the catalyst which would limit the conversion to the equilibrium of the reaction system components.

The overhead consisting of unreacted benzene, any unreacted ethylene and the inert aliphatic compounds are partially condensed in condenser 22 to separate the ethylene as a gas from the liquid containing the unreacted benzene and most of the inert aliphatic compounds ($C_{3+}$) in accumulator 23. A portion of the benzene, along with any aliphatic compounds contained therein, is returned to the primary distillation column reactor 2 as reflux via line 204. The remainder of the liquid and gas from the accumulator-separator are fed to the secondary distillation column reactor 1 in much the same configuration as the primary column. The gas is fed to the secondary column 1 via line 202 to a point below the catalyst bed 11 and the liquid fed via line 204 to a point above the secondary bed 11.

In the secondary column 1 additional aliphatic compounds, herein $nC_5$, $nC_6$ and $iC_6$, are injected into the upper portion 12 as reflux from accumulator 15 via line 104. A convenient stream for this particular use is the overhead from a deisohexanizer operating on a petroleum distillate stream. While the principles of distillation discussed above apply, the addition of the aliphatic compound operates to simply fill the upper portion 12 of the secondary column 1 with aliphatic "distillation" and forces the benzene and alkylated product, ethyl benzene, to the lower portion 13 of the secondary column where they may be recovered as bottoms via line 106. The bottoms from the secondary column are then recycled to the primary column 2 via line 106 as shown where the ethyl benzene is recovered with the bottoms there and the benzene contributes to the molar excess required for the primary reaction.

After initial start up and the desired equilibrium is reached in the secondary column, aliphatic material is withdrawn via line 105 at the rate of addition in the gaseous and benzene charge to the primary column 2. Inert ethane, $C_2$, is vented via line 102 as, for example to refinery fuel.

While the molecular sieves which comprises the primary and secondary distillation reaction zones may be identical, this may not always be desirable. In another embodiment cumene is produced by the alkylation of benzene with propylene. The process is similar with propylene being substituted for the ethylene. However, in this process the catalyst beds in the primary and secondary distillation reaction zones consist of a Y type molecular sieve and an Omega type molecular sieve respectively. Such a dual bed reaction system has been previously described in a commonly assigned U.S. patent application Ser. No. 07/385,443 filed July 26, 1989.

The invention claimed is:

1. A process for alkylating an organic aromatic compound with a lower boiling olefin wherein inert aliphatic compounds are contained in either the olefin or organic aromatic feed streams or both, comprising:
    (a) contacting a molar excess of said organic aromatic compound with said olefin in a first distillation column reactor containing a first fixed bed molecular sieve characterized as an acidic catalytic distillation structure in a first distillation reaction zone thereby concurrently:
        (i) reacting at least a portion of said organic aromatic compound with a portion of said olefin to form a first reaction mixture containing an alkylation product, unreacted organic aromatic compound, unreacted olefin and inert aliphatic compounds, and
        (ii) distilling said first reaction mixture to produce a first bottoms product containing substantially pure alkylation product and a first overhead containing substantially all of said unreacted organic aromatic compound, unreacted olefin, and inert aliphatic compounds;
    (b) partially condensing said first overhead to produce a liquid stream containing substantially all of said unreacted organic aromatic compound and substantially all of said aliphatic compound boiling above $C_2$ and a gas stream containing substantially all of said unreacted olefin and the remainder of said aliphatic compounds;
    (c) contacting said liquid and gas streams in a second distillation column reactor containing a second fixed bed molecular sieve characterized as an acidic catalytic distillation structure in a second distillation reaction zone thereby concurrently:
        (i) reacting at least a portion of said unreacted organic aromatic compound with the remainder of said olefin to form a second reaction mixture containing an alkylation product, unreacted organic aromatic compound, and inert aliphatic compounds, and
        (ii) distilling said second reaction mixture to separate said unreacted organic aromatic compound and said alkylation product from said aliphatic compound; and
    (d) initially injecting additional aliphatic compound into said second distillation column reactor as reflux to allow said second distillation column to operate at an equilibrium wherein substantially only aliphatic compound is taken as a second overhead and substantially only unreacted organic aromatic compound and alkylation product is taken as a second bottoms.

2. The process according to claim 1 wherein said second bottoms is recycled to said first distillation column reactor wherein the alkylation product contained therein is recovered with said first bottoms and said unreacted organic aromatic compound contributes to said molar excess.

3. The process according to claim 1 wherein said organic aromatic compound is benzene, said olefin is ethylene and said alkylation product is ethyl benzene.

4. The process according to claim 3 wherein said aliphatic compound injected in step (d) comprises normal propane, butane, pentane, hexane, isohexane or mixtures thereof.

5. The process according to claim 3 wherein both of said fixed bed molecular sieves contain identical molecular sieves.

6. The process according to claim 1 wherein said organic aromatic compound is benzene, said olefin is propylene and said alkylation product is cumene.

7. The process according to claim 6 wherein said first bed consists of a Y molecular sieve and said second fixed bed consists of an Omega molecular sieve.

8. A process for producing ethyl benzene by alkylating benzene with ethylene contained wherein inert aliphatic compounds are contained in either the ethylene feed stream, the benzene feed stream or both, comprising:
 (a) contacting a molar excess of said benzene with said ethylene in a first distillation column reactor containing a first fixed bed molecular sieve characterized as an acidic catalytic distillation structure in a first distillation reaction zone thereby concurrently:
  (i) reacting at least a portion of said benzene with a portion of said ethylene to form a first reaction mixture containing ethyl benzene, benzene, unreacted ethylene and inert aliphatic compounds, and
  (ii) distilling said first reaction mixture to produce a first bottoms product containing substantially pure ethyl benzene and a first overhead containing substantially all of said unreacted benzene, unreacted ethylene, and inert aliphatic compounds;
 (b) partially condensing said first overhead to produce a liquid stream containing substantially all of said unreacted benzene and all of said aliphatic compound boiling above $C_2$ and a gas stream containing substantially all of said unreacted ethylene and the remainder of said aliphatic compounds;
 (c) contacting said liquid and gas streams in a second distillation column reactor containing a second fixed bed molecular sieve characterized as an acidic catalytic distillation structure in a second distillation reaction zone thereby concurrently:
  (i) reacting at least a portion of said unreacted benzene with the remainder of said unreacted ethylene to form a second reaction mixture containing ethyl benzene, unreacted benzene, and inert aliphatic compounds, and
  (ii) distilling said second reaction mixture to separate said unreacted benzene and said ethyl benzene from said aliphatic compound; and
 (d) initially injecting additional aliphatic compound into said second distillation column reactor as reflux to allow said second distillation column to operate at an equilibrium wherein only aliphatic compound is taken as a second overhead and only unreacted benzene and ethyl benzene is taken as a second bottoms.

9. The process according to claim 8 wherein said second bottoms is recycled to said first distillation column reactor wherein the ethyl benzene contained therein is recovered with said first bottoms and said unreacted benzene contributes to said molar excess.

10. A process for producing cumene by alkylating benzene with propylene contained wherein inert aliphatic compounds are contained either the propylene feed stream, the benzene feed stream or both, comprising:
 (a) contacting a molar excess of said benzene with said propylene in a first distillation column reactor containing a first fixed bed consisting of a Y molecular sieve characterized as an acidic catalytic distillation structure in a first distillation reaction zone thereby concurrently:
  (i) reacting at least a portion of said benzene with a portion of said propylene to form a first reaction mixture containing cumene, unreacted benzene, unreacted propylene and inert aliphatic compounds, and
  (ii) distilling said first reaction mixture to produce a first bottoms product containing substantially pure cumene and a first overhead containing substantially all of said unreacted benzene, unreacted propylene, and inert aliphatic compounds;
 (b) partially condensing said first overhead to produce a liquid stream containing substantially all of said unreacted benzene and all of said aliphatic compound boiling above $C_2$ and a gas stream containing substantially all of said unreacted propylene and the remainder of said aliphatic compounds;
 (c) contacting said liquid and gas streams in a second distillation column reactor containing a second fixed bed consisting of an Omega molecular sieve characterized as an acidic catalytic distillation structure in a second distillation reaction zone thereby concurrently:
  (i) reacting at least a portion of said unreacted benzene with the remainder of said propylene to form a second reaction mixture containing cumene, unreacted benzene and inert aliphatic compounds, and
  (ii) distilling said second reaction mixture to separate said unreacted benzene and said cumene from said aliphatic compound; and
 (d) initially injecting additional aliphatic compound into said second distillation column reactor as reflux to allow said second distillation column to operate at an equilibrium wherein only aliphatic compound is taken as a second overhead and only unreacted benzene and cumene is taken as a second bottoms.

11. The process according to claim 10 wherein said second bottoms is recycled to said first distillation column reactor wherein the cumene contained therein is recovered with said first bottoms and said unreacted benzene contributes to said molar excess.

* * * * *